United States Patent
Goerne

(10) Patent No.: US 7,994,142 B2
(45) Date of Patent: Aug. 9, 2011

(54) AGENTS CONTAINING FOLIC ACID, VITAMIN B6 AND VITAMIN B12, AND THE USE THEREOF

(75) Inventor: Martin Goerne, Hamburg (DE)

(73) Assignee: Phrontier S.A.R.L., Caudebec-en-Caux (FR)

(*) Notice: Subject to any disclaimer, the term of this patent is extended or adjusted under 35 U.S.C. 154(b) by 0 days.

(21) Appl. No.: 11/813,729

(22) PCT Filed: Jan. 11, 2006

(86) PCT No.: PCT/EP2006/000198
§ 371 (c)(1),
(2), (4) Date: Dec. 27, 2007

(87) PCT Pub. No.: WO2006/074918
PCT Pub. Date: Jul. 20, 2006

(65) Prior Publication Data
US 2009/0253649 A9    Oct. 8, 2009

(30) Foreign Application Priority Data
Jan. 12, 2005 (DE) .......... 10 2005 001 479

(51) Int. Cl.
A61K 31/7056 (2006.01)
A61K 31/28 (2006.01)
A61K 31/409 (2006.01)
A61K 31/4415 (2006.01)
A61K 31/5025 (2006.01)
C07F 15/06 (2006.01)
C07D 487/06 (2006.01)
C07D 213/30 (2006.01)

(52) U.S. Cl. .......... 514/43; 514/501; 514/350; 514/351; 514/249; 556/140; 556/146; 556/138; 544/258; 546/298; 546/300

(58) Field of Classification Search .......... None
See application file for complete search history.

(56) References Cited

U.S. PATENT DOCUMENTS

| 5,563,126 A | 10/1996 | Allen et al. |
| 5,932,624 A | 8/1999 | Herbert |
| 6,129,918 A | 10/2000 | Amagase |
| 6,207,651 B1 | 3/2001 | Allen et al. |
| 6,210,686 B1 | 4/2001 | Bell et al. |
| 6,274,170 B1 | 8/2001 | Heibel et al. |
| 6,297,224 B1 | 10/2001 | Allen et al. |
| 6,299,896 B1 | 10/2001 | Cooper et al. |
| 2003/0225030 A1 | 12/2003 | Allen et al. |
| 2005/0032740 A1 | 2/2005 | Venkataraman |
| 2005/0222079 A1 | 10/2005 | Goerne |

FOREIGN PATENT DOCUMENTS

| DE | 43 26 698 A1 | 3/1995 |
| EP | 0 595 005 A1 | 5/1994 |
| WO | WO 03/068231 A2 | 8/2003 |

OTHER PUBLICATIONS

Naurath et al.(I), "Effects of Vitamin B12, Folate, and Vitamin B6 Supple-ments in Elderly People with Normal Serum Vitamin Concentrations," The Lancet, 346, 85-89 (Jul. 8, 1995).*
Naurath et al.(II), "Does a Single Vitamin B-Supplementation Induce Functional Vitamin B-Deficiency?" Clinical Chemistry and Laboratory Medicine, 39(8), 768-771 (2001).*
Beers et al. (eds.), Chapter 202 in The Merck Manual of Diagnosis and Therapy, 17th Edition, Merck & Co., Inc., Rahway, NJ, Jan. 1999, only text pp. 1658-1659 have been supplied by applicant.*
Bostom et al., "High dose B-vitamin treatment of hyperhomocysteinemia in dialysis patients" Kidney International (1996) vol. 49 pp. 147-152.*
Bleie et al., "Changes in basal and postmethionine load concentrations of total homocysteine and cystathionine after B vitamin intervention" American Journal of Clinical Nutrition (2004) vol. 80 pp. 641-648.*
Marcucci et al., "Homocysteine-Lowering Therapy and Carotid Intima-Media Thickness in Renal Transplant Recipients" Transplantation Proceedings (2005) vol. 37 pp. 2491-2492.*

* cited by examiner

*Primary Examiner* — Eric S Olson
(74) *Attorney, Agent, or Firm* — Oblon, Spivak, McClelland, Maier & Neustadt, L.L.P.

(57) ABSTRACT

The invention relates to agents that contain folic acid, vitamin B6 and vitamin B12, and to the use thereof in hyperhomocysteinemia for controlling homocysteine levels. The agents are mainly suitable for the preventive and acute treatment of vascular diseases, of pregnant women and neurodegenerative diseases and are particularly advantageous in cases where the homocysteine levels to be controlled are found in an individual suffering from renal failure or being treated with immune suppressors. The invention particularly relates to pharmaceutical agents and food supplements comprising a corresponding active ingredient combination and to agents in the form of commercial packages containing corresponding combination preparations or monopreparations for the combined use.

3 Claims, No Drawings

AGENTS CONTAINING FOLIC ACID, VITAMIN B6 AND VITAMIN B12, AND THE USE THEREOF

The present invention relates to compositions comprising folic acid, vitamin B6 and vitamin B12, and to the use thereof for regulating homocysteine levels. The compositions can thus be used in particular for the preventive and acute treatment of vascular disorders. Descriptions are given in particular of pharmaceutical compositions and food supplements with a corresponding active ingredient combination, and compositions in the form of commercial packs with corresponding combination products or single-ingredient products for combined use.

It has recently been disclosed that homocysteine is a risk factor for coronary, peripheral and cerebral vascular disorders. Patients with hereditary hyperhomocysteinemia, an autosomal recessive disorder, have homocysteine plasma levels which are about 10-20 times higher than the normal levels. In children affected by the homozygous form of the disorder, vascular lesions become evident at an early date and represent the main cause of the frequently fatal outcome of the disorder in childhood. Whereas elevated homocysteine levels in the genetically related forms of hyperhomocysteinemia are usually attributable to a deficiency of cystathionine β-synthase and/or a mutation in 5,10-methylenetetrahydrofolate reductase, it is also possible for alterations in folic acid, vitamin B6, vitamin B12 and betaine metabolism to lead to elevated homocysteine levels. Accordingly, acquired types of hyperhomocysteinemia may also occur. For example, renal failure or a deficiency of folic acid, cobalamin and/or pyridoxine or metabolites thereof may lead no elevated homocysteine levels. Especially in elderly people, such a vitamin deficiency, which may be caused by an inadequate intake or by malabsorption, is regarded as the most frequent cause of acquired hyperhomocysteinemia.

Vitamin B12 is necessary in order to transfer a 1-carbon unit on folic acid to homocysteine and to convert the latter into methionine. Vitamin B6 is involved in a further metabolic pathway for the degradation of excess homocysteine.

It has already been proposed to employ a wide variety of folic acid, vitamin B6 and vitamin B12 containing vitamin products to reduce elevated homocysteine levels.

For example, U.S. Pat. No. 5,932,624 describes a composition which contains 500 μg of folic acid, 25 μg of vitamin B12 and 10 mg of vitamin B6. Depending on the patient's condition, in general 300 to 2000 μg of folic acid, 25 to 1000 μg of vitamin B12 and 5 to 20 mg of vitamin B6 should be administered for the homocysteine plasma levels to fall to normal levels.

The combination indicated in U.S. Pat. No. 6,274,170 of vitamins and aspirin for the treatment of atherosclerotic cardiovascular disorders contains 400 to 1000 μg of folic acid, 3 to 25 mg of vitamin B6 and 5 to 500 μg of vitamin B12.

A multivitamin and mineral supplement which, besides a number of other vitamins and essential trace elements, contains 800 μg of folic acid, 25 mg of vitamin B6 and 400 μg of vitamin B12 is described in U.S. Pat. No. 6,299,696. This composition is also said to be able to reduce the homocysteine levels.

Daily intake of ISO to 800 μg of folic acid, 1.6 to 4.6 mg of vitamin B6 and 1.5 to 4.0 μg of vitamin B12 together with β-glucan- or glucomannan-containing fibers is recommended in U.S. Pat. No. 6,210,686 in order to improve the composition of serum lipids, to reduce homocysteine levels and to protect lipoproteins from oxidation.

According to U.S. Pat. No. 6,297,224, and U.S. Pat. No. 6,207,651 and U.S. Pat. No. 5,563,126 which are related thereto, vitamin preparations which contain 0.4 mg or 1.0 mg of folic acid together with 25 mg of vitamin B6 and 2.0 mg of vitamin B12 are to be employed for the prevention and treatment of elevated homocysteine, cystathionine, methylmalonic acid or 2-methylcitric acid serum levels.

U.S. Pat. No. 6,129,918 describes a garlic-based composition for reducing homocysteine plasma levels. In addition to garlic or garlic extract, this composition may comprise folic acid, vitamin B6 and vitamin B12. The last three active ingredients mentioned are in this case intended to enhance the advantageous properties of garlic.

WO 03/068231 relates to compositions which comprise folic acid, vitamin B6 and vitamin B12, and to the use thereof for regulating homocysteine levels. The quantitative ratio of folic acid to vitamin B6 and of vitamin B12 to vitamin B6 is stated to be in a range from about 1:67 to 1:150 by weight, and the quantitative ratio of folic acid to vitamin B12 is stated to be in a range from about 1:0.67 to 1:1.50 by weight. These compositions have a reliable effect lowering homocysteine levels. It has, however, been found that although in certain disorders such as chronic renal failure and the dialysis treatment associated therewith, or in patients treated with immunosuppressants, elevated homocysteine levels can be reduced, they often cannot be returned to a normal extent.

It has now been found that the combined use of folic acid, vitamin B6 and vitamin B12 in particular quantities surprisingly reduces the homocysteine level in certain cases even more effectively and thus the risk of vascular disorders in particular in certain patient groups can be reduced even further than with the previously disclosed combinations of folic acid, vitamin B6 and vitamin B12.

The present invention therefore relates to compositions based on folic acid, vitamin B6 and vitamin B12 or physiologically acceptable derivatives and/or salts thereof, characterized in that the quantitative ratios of folic acid to vitamin B6 is in a range from about 1:5 to about 1:15, the quantitative ratio of vitamin B12 to vitamin B6 is in a range from about 1:50 to about 1:125, and the quantitative ratio of folic acid to vitamin B12 is in a range from about 1:0.05 to about 1:0.25.

The inventive compositions based on folic acid, physiologically acceptable derivatives or salts thereof (also referred to for simplicity as "folic acids" or "folic acid component"), vitamin B6, physiologically acceptable derivatives or salts thereof (also referred to for simplicity as "B6 vitamins" or "vitamin B6 component") and vitamin B12, physiologically acceptable derivatives or salts thereof (also referred to for simplicity as "B12 vitamins" or "vitamin B12 component") offer considerable advantages in regulating homocysteine levels and thus in the preventive and acute treatment of vascular disorders.

The present invention therefore also relates to the use of the inventive combination of folic acid, vitamin B6 and vitamin B12 or physiologically acceptable derivatives and/or salts thereof for regulating the homocysteine level. The regulation relates in particular in the acute sphere to the reduction of elevated homocysteine levels, i.e. in particular the treatment of hyperhomocysteinemia, and in the prophylactic sphere to the prevention of elevated homocysteine levels and the maintenance of normal homocysteine levels. The regulation of homocysteine levels is associated in particular with a prophylactic treatment of disorders connected with elevated homocysteine levels, i.e. especially those accompanied or caused by elevated homocysteine levels.

The present invention therefore further relates to the use of the inventive combination of folic acid, vitamin B6 and vitamin B12 or physiologically acceptable derivatives and/or salts thereof for treating disorders which are connected with an elevated homocysteine level. These include in particular vascular disorders such as arteriosclerosis, venous thromboses and arterial occlusions, fetal damage such as neural tube defects, and neurodegenerative disorders such as certain types of Alzheimer's dementia.

In this sense, the invention also relates to compositions for regulating the homocysteine level and for treating disorders which are connected with elevated homocysteine levels. These compositions are based on the inventive active ingredient combination and, where appropriate, further active ingredients, it being preferable for the active ingredients or active ingredient components to be formulated together in one formulation or separately in at least two or three different formulations.

Particular advantages of use of the active ingredient combination of the invention emerge in certain patient groups in which although the homocysteine levels are reduced, they are not normalized, with known compositions. These include in particular individuals with renal failure and those treated with immunosuppressants.

Preferred compositions and uses are those in which the quantitative ratio of folic acid to vitamin B6 is in a range from about 1:6 to about 1:14.5, the quantitative ratio of vitamin B12 to vitamin B6 is in a range from about 1:52.5 to about 1:116, and the quantitative ratio of folic acid to vitamin B12 is in a range from about 1:0.07 to about 1:0.20.

Advantageous compositions and uses are those in which the quantitative ratio of folic acid to vitamin B6 is in a range from about 1:6 to about 1:12, the quantitative ratio of vitamin B12 to vitamin B6 is in a range from about 1:53 to about 1:97, and the quantitative ratio of folic acid to vitamin B12 is in a range from about 1:0.09 to about 1:0.16.

Particularly advantageous compositions and uses are those in which the quantitative ratio of folic acid to vitamin B6 is in a range from about 1:6 to about 1:10, the quantitative ratio of vitamin B12 to vitamin B6 is in a range from about 1:53 to about 1:83, and the quantitative ratio of folic acid to vitamin B12 is in a range from about 1:0.11 to about 1:0.14.

In this connection, the stated quantitative ratios relate to quantities by weight of the active ingredients folic acid, vitamin B6 and vitamin B12, so that an appropriate conversion must take place where necessary for salts and derivatives. This applies analogously to the active ingredient contents indicated in the present description. Alternatively, the ratios can also be based on molar quantities, so than on the assumption that one mole of the relevant derivative or salt comprises one mole of folic acid, vitamin B6 or vitamin B12, the molar quantitative ratios for folic acid, vitamin B6, vitamin B12 and their derivatives and/or salts can be expressed uniformly.

"Folic acid" refers according to the invention to N-pteroyl-glutamic acid of the formula I

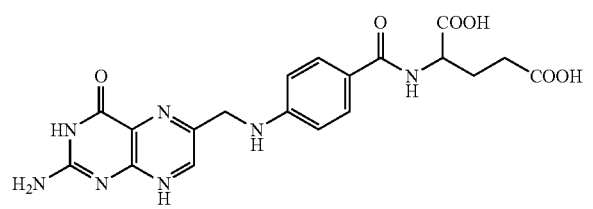

including the optical isomers covered by this formula, both as mixtures, e.g. as racemate, and in pure form, e.g. R or S enantiomers. N-Pteroyl-L-glutamic acid of the formula Ia

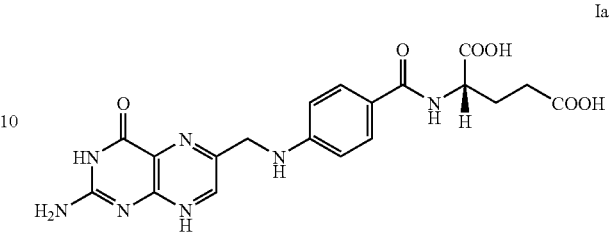

is preferred. The folic acid derivatives include in particular folic acid metabolites, amides and esters of folic acid, as well as the metabolites. Amides and esters which can be hydrolyzed under physiological conditions, such as amides with $C_1$-$C_{10}$-alkylamines or esters with $C_1$-$C_{10}$-alcohols are advantageous. A particular form of the amides are N-pteroylpolyglutamic acids.

The folic acid metabolites include in particular $H_4$-folic acids of the formula Ib

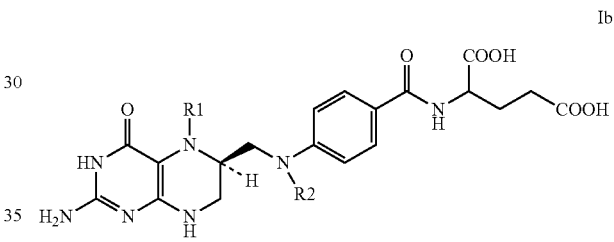

in which R1 is hydrogen, methyl, —HC=O (formyl) or —HC=NH (formimino), and R2 is hydrogen or —HC=O (formyl), or R1 and R2 together form a methylene or methenyl bridge. The optical isomers covered by this formula are included in accordance with the above statements, with preference for the L-glutamic acid derivatives in this case too. Particular mention should be made of tetrahydrofolic acid, 5-methyltetrahydrofolic acid, 5,10-methylenetetrahydrofolic acid, 5-formyltetrahydrofolic acid, 10-formyltetrahydrofolic acid, 5-formiminotetrahydrofolic acid and 5,10-methenyltetrahydrofolic acid.

The physiologically acceptable salts of folic acid and folic acid derivatives include acid and base addition salts and appropriate mixed forms.

The acid addition salts include salts of folic acid or folic acid derivatives with inorganic acids such as hydrochloric acid, sulfuric acid, nitric acid or phosphoric acid, or organic acids, in particular carboxylic acids, e.g. acetic acid, tartaric acid, lactic acid, citric acid, malic acid, mandelic acid, ascorbic acid, maleic acid, fumaric acid, gluconic acid or sulfonic acids, e.g. methanesulfonic acid, benzenesulfonic acid and toluenesulfonic acid, and the like.

The base addition salts include salts of folic acid or folic acid derivatives with inorganic bases, for example metal hydroxides or carbonates of alkali metals, alkaline earth metals or transition metals, or with organic bases, for example ammonia or basic amino acids such as arginine and lysine, amines, e.g. methylamine, dimethylamine, trimethylamine, triethylamine, ethylamine, diethylamine, ethylene-diamine, ethanolamine, diethanolamine, 1-amino-2-propanol, 3-amino-1-propanol or hexamethylenetetramine, saturated cyclic amines having 4 to 6 ring carbon atoms, such as piperidine, piperazine, pyrrolidine and morpholine, and further organic bases, for example N-methylglucamine, creatine and tromethamine, and quaternary ammonium compounds such as tetramethylammonium and the like.

Salts with inorganic bases are preferred, e.g. Na, K, Mg, Ca, Zn, Cr and Fe folates.

"Vitamin B6" designates according to the invention 4,5-bis(hydroxymethyl)-2-methyl-3-pyridinol of the formula II

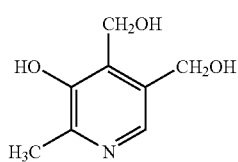

also referred to as pyridoxine (INN).

The vitamin B6 derivatives include in particular pyridoxals and pyridoxamines, and esters of pyridoxines, pyridoxals and pyridoxamines. Also advantageous in this case are esters which can be hydrolyzed under physiological conditions.

Particular mention should be made in this connection of the pyridoxines, pyridoxals and pyridoxamines of the formula IIa

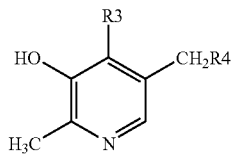

in which $R_3$ is $CH_2OH$, CHO or $CH_2NH_2$, and $R_4$ is OH or $OPO_3H_2$.

Physiologically acceptable salts of vitamin B6 or vitamin B6 derivatives include in particular acid addition salts, e.g. with the abovementioned inorganic and organic acids. Particular mention should be made of the hydrochloride, especially pyridoxine HCl.

"Vitamin B12" is also referred to as cyanocobalamin or cobalamin.

Vitamin B12 derivatives include in particular cobalamins in which the cyano group of the cyanocobalamin is replaced by other cobalt coordination partners. These include in particular hydroxocobalamin, aquocobalamin, nitrosocobalamin, methylcobalamin and adenosylcobalamin (coenzyme B12).

Physiologically acceptable salts of vitamin B12 or vitamin B12 derivatives include in particular acid addition salts, e.g. with the abovementioned inorganic and organic acids. The acetate of hydroxocobalamin should be mentioned in particular.

Folic acids, B6 and B12 vitamins are sufficiently well known and can be either purchased or made available in a manner known per se.

Besides the folic acid, vitamin B6 and vitamin B12 components, the inventive compositions may include further active ingredients. These active ingredients may be in particular those whose effect is similar to the effect mediated by folic acid, vitamin B6 and vitamin B12 or supplements the latter and which in particular complies with the inventive purposes of use. Thus, in addition to the inventive combination, it may be advantageous to administer active ingredients which lower the homocysteine level, antithrombotics, antisclerotics and the like.

Assays for determining homocysteine levels, which are normally in the range from 5 to 15 μmol/l of blood plasma, are known (cf. for example the prior art described at the outset). Elevated homocysteine levels are referred to as hyperhomocysteinemia. Elevated homocysteine levels can be reduced or preventively averted with the aid of the inventive compositions.

Depending on the homocysteine level, hyper-homocysteinemias are divided into three classes:

Mild hyperhomocysteinemias are characterized by homocysteine levels in a range from more than 15 and up to 30 μmol/l of blood plasma.

Moderate hyperhomocysteinemias are characterized by homocysteine levels in the range from more than 30 and up to 100 μmol/l of blood plasma.

High hyperhomocysteinemias are characterized by homocysteine levels of more than 100 μmol/l of blood plasma.

Particular advantages emerge according to the invention in relation to the treatment of moderate hyperhomocysteinemias.

The present invention is directed in particular to the treatment of one or more of the following pathological states:

Hereditary hyperhomocysteinemia. The pathological state of hereditary hyperhomocysteinemia is characterized by genetically related disturbances of homo cysteine metabolism. Metabolic disturbances of this type include in particular an absence (homozygous form) or deficiency (heterozygous form) of cystathionine β-synthase, a deficiency of methylenetetrahydrofolate reductase, a mutation-related modification of methylenetetrahydrofolate reductase into a thermolabile derivative thereof, and a number of other alterations in folic acid, vitamin B6, vitamin B12 and betaine metabolism. The signs and symptoms of hereditary hyperhomocysteinemia include homocysteinuria, mental retardation, dislocation of the lens of the eye, skeletal abnormalities and/or vascular disorders, which can thus be treated acutely or preventively according to the invention as symptom or syndrome.

Acquired hyperhomocysteinemia. Acquired types of hyperhomocysteinemia are usually characterized by manifestations of deficiency which lead to accumulation of homocysteine. For example, deficiencies of folic acid and folic acid derivatives, vitamin B12 and vitamin B12 derivatives, vitamin B6 and vitamin B6 derivatives, and a general vitamin deficiency, may lead to elevated homocysteine levels. It is moreover possible for the vitamin deficiency to be caused for example by an inadequate intake or by malabsorption of the respective vitamin(s). Elevated homocysteine levels may also be caused by medicaments able to influence folic acid metabolism, such as methotrexate or anticonvulsants; able to influence vitamin B12 metabolism, such as nitrates; or able to influence vitamin B6 metabolism, such as theophylline. In addition, the homocysteine plasma level is influenced by age, gender, cigarette smoking, essential hypertension, hypercholesterolemia and insufficient exercise.

The present invention is additionally directed at the treatment of disorders which are connected with elevated homocysteine levels, in particular are associated therewith or caused thereby. These include in particular vascular disorders, fetal malformations and certain neurodegenerative disorders. Prevention is particularly important in this area of indications.

Vascular disorders means disorders of the peripheral, coronary and cerebral vessels. Particular mention should be made of alterations in vascular endothelial cells, proliferation of muscle cells and/or thickening of the intima of vessels. It is thus possible to treat according to the invention in particular arterio-scleroses, venous thromboses, arterial occlusions and further arteriovenous vascular disorders.

Fetal malformations, especially neural tube defects, may occur if the mother suffers from elevated homocysteine levels during pregnancy.

Elevated homocysteine levels may also be involved in neurodegenerative disorders, especially vascular forms of dementia in the elderly.

The invention is thus directed according to a particular aspect at reducing the risk of the occurrence of the vascular disorders, fetal malformations and neurodegenerative disorders described above.

Particular advantages of a use of the active ingredient combination of the invention emerge in certain patient groups in which although the homocysteine levels are reduced, they are not normalized, with known compositions.

These include in particular individuals with renal failure. Renal failure means according to the invention that the elimination efficiency of the kidney is inadequate or absent. These include individuals with a creatinine clearance $CL_{CR}$ of less than 100 ml/min, especially less than 50 ml/min and in particular less than 10 ml/min. The use of the active ingredient combination of the invention is directed in particular at the treatment of individuals with chronic renal failure. These are individuals whose renal elimination efficiency is permanently inadequate or absent. In this case, regular hemodialysis is required. The use according to the invention is very particularly preferred for individuals with advanced chronic renal failure (also referred to as terminal renal failure TRF; also: end stage renal disease ESRD) and accordingly on average with hemodialysis at least twice and in particular about three times a week.

The patient groups which can be treated advantageously include those which will undergo, are undergoing or have undergone an immunosuppressant therapy, individuals treated with immunosuppressants are for example those suffering from an autoimmune disease or an immunoproliferative disorder, or have received a transplant. Autoimmune diseases include for example lupus (lupus erythematosus, lupus nephritis), Hashimoto's thyroiditis, primary myxedemas, Basedow's disease, pernicious anemia, autoimmune atrophic gastritis, Addison's disease, diabetes (e.g. insulin-dependent diabetes mellitus, type I diabetes mellitus), Goodpasture's syndrome, myasthenia gravis, pemphigus, Crohn's disease, sympathetic ophthalmia, autoimmune uveitis, multiple sclerosis, autoimmune hemolytic anemia, idiopathic thrombocytopenia, primary biliary cirrhosis, chronic hepatitis, ulcerative colitis, Sjögren's syndrome, rheumatic disorders (e.g. rheumatoid arthritis), polymyositis, scleroderma and mixed connective tissue disorders. Immunoproliferative disorders include for example psoriasis, T-cell lymphomas, acute lymphoblastic T-cell leukemia, testicular angiocentric T-cell lymphomas and benign lymphocytic angiitis. Transplant-related disorders include graft versus host disease (GVHD) (e.g. as a consequence of a bone marrow transplantation or of a tolerance induction), disorders associated with acute and/or chronic rejection of one of tissue or cell transplants, allografts or xenografts.

The therapeutic immunosuppressants normally administered include calcineurin inhibitors such as cyclosporin and FK506, alkylating active ingredients such as cyclophosphamide, DHFA reductase inhibitors such as methotrexate, azathioprine, chloroquine, hydroxychloroquine, sulphasalazine, leflunomide, gold salts, penicillamine, cytokine blockers, e.g. IL-1 antagonists such as anakinra and AMG719, TNFα atagonists such as infliximab, etanercept and humira, TNF receptor antagonists such as pegsunercept, LFA-1 antagonists such as efalizumab, steroids, e.g. corticosteroids and in particular glucocorticoids such as prednisone, NSAIDs such as acetylsalicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, meloxicam, codeine phosphate, propoxyphene napsylate, oxycodone hydrochloride, oxycodone bitartrate and tramadol, a large number of proteins directed against surface proteins of lymphocytes, such as antibodies and fusion proteins, VLA4 antagonists, selectin antagonists, rapamycin 40-O-(2-hydroxy)ethylrapamycin, mizoribine, mycophenolic acid, mycophenolate mufetil, 15-deoxysper-gualine, tacrolimus, basiliximab, Cytoxan, interferon-β-1a, interferon-β-1b, glatiramer acetate and mitoxantrone hydrochloride.

The inventive compositions and uses become increasingly important in adults with increasing age. The treatment has particular advantages in the group of over 40s and especially the over 50s. The inventive treatment is indicated in particular when there is evidence of arterioscleroses, arterial occlusions, venous thromboses and/or vascular forms of dementia in the elderly, or there is a risk of these disorders. A further group in which the inventive treatment may have particular advantages are children with hereditary hyperhomocysteinemia, and pregnant women, even if there is no evidence of vascular disorders and the homocysteine levels are only slightly elevated.

According to the invention, the individual to be treated, preferably a mammal, especially a human and also a productive or domestic animal, receives administration of an effective amount of the inventive active ingredient combination of folic acid component, vitamin B6 component and vitamin B12 component, usually formulated in accordance with pharmaceutical, veterinary or food technological practice. An amount is effective according to the invention especially when it brings about a significant reduction in the homocysteine level, advantageously into the normal range.

The treatment usually takes place by single or multiple daily administration of a single dose, where appropriate together or alternately with other active ingredients or active ingredient-containing products, so that an individual to be treated with the weight of an average adult of about 75 kg usually receives administration of a minimum daily dose of about 4 mg, preferably about 5 mg and advantageously about 6 mg, of folic acid; of about 42 mg, e.g. of about 45 mg or of about 50 mg, of vitamin B6; and of about 0.5 mg, preferably about 0.6 mg and advantageously about 0.7 mg, of vitamin B12. According to another aspect, the maximum daily dose is usually about 7 mg, e.g. about 6.5 mg or about 6 mg, of folic acid; about 58 mg, e.g about 55 mg or about 50 mg, of vitamin B6; and about 0.8 mg, e.g. 0.75 mg or about 0.7 mg, of vitamin B12. Accordingly, the maximum daily doses are in the range of 4 to 7 mg, preferably 5 to 7 mg and in particular 6 to 7 mg of folic acid; 42 to 58 mg of vitamin B6; and 0.5 to 0.8 mg, preferably 0.6 to 0.8 mg and in particular 0.7 to 0.8 mg of vitamin B12. The daily dose should be adjusted appropriately if the weight differs from the average. This adjustment takes place in a conventional way by the skilled worker, if necessary taking account of analytical investigations. In addition, differences in the daily dose prescribed by the physician may also arise owing to the state of health of the individual to be treated.

The treatment usually takes place over an appropriate period in the region of days or weeks. It is expedient to normalize the homocysteine levels within a treatment period of about 1 to 4 weeks. If necessary, the treatment is also continued after the homocysteine levels have normalized. This applies in particular to the hereditary types of hyperhomocysteinemia and acquired types in which a causative treatment is not possible or has no success, and discontinuation of the inventive treatment would result in a renewed rise in the homocysteine levels.

The invention also relates to the production of compositions for the treatment of an individual, preferably a mammal, in particular a human and also a productive or domestic animal.

The compositions include in particular pharmaceutical compositions, food supplements and food products, e.g. functional or dietetic food products. The inventive food products have, besides a function predominantly related to nutritional value, additionally a function related to the active ingredients and particularly related to the inventive active ingredient combination. They are therefore referred to as functional or dietetic food or nutritional products. Food supplements serve to supplement the daily diet with the inventive active ingredient combination, in which case the function related to the nutritional value of the food supplement becomes less important as such.

According to one aspect, the present invention relates to formulations comprising
i) at least one active ingredient from the folic acid group (folic acid, physiologically acceptable derivatives and/or salts thereof),
ii) at least one active ingredient from the vitamin B6 group (vitamin B6, physiologically acceptable derivatives and/or salts thereof), and
iii) at least one active ingredient from the vitamin B12 group (vitamin B12, physiologically acceptable derivatives and/or salts thereof), and
where appropriate an least one further active ingredient and a formulation base, in the quantitative ratios indicated according to the invention.

Thus, the active ingredient combination comprises for the purposes of the invention as active ingredient component i) folic acid, a physiologically acceptable derivative and/or salt thereof. Mixtures of these forms are possible but are to be considered only in particular cases. According to a particular embodiment, active ingredient component i) consists of at least 90% by weight folic acid.

The active ingredient combination additionally comprises for the purposes of the invention as active ingredient component ii) vitamin B6, a physiologically acceptable derivative and/or salt thereof. Mixtures of these forms are likewise possible, but are to be considered only in particular cases. According to a particular embodiment, active ingredient component ii) consists of at least 90% by weight pyridoxine HCl.

The active ingredient combination additionally comprises for the purposes of the invention as active ingredient component iii) vitamin B12, a physiologically acceptable derivative and/or salt thereof. Mixtures of these forms are likewise possible, but are to be considered only in particular cases. According to a particular embodiment, active ingredient component iii) consists of at least 90% by weight cobalamin.

The content of the active ingredient combination in the formulation is larger than the content present where appropriate in natural sources, in particular food products. In this sense, the inventive compositions are fortified in relation to the active ingredient combination. The content of active ingredient combination of i), ii) and iii) in the formulation is preferably at least about 0.01% by weight, advantageously at least about 0.05% by weight and in particular at least about 0.1% by weight. In the case of a pharmaceutical composition, the content is usually about 1 to 60% by weight, preferably about 5 to 35% by weight, and in particular about 10 to 30% by weight, and in the case of a food supplement and especially in the case of food products where appropriate correspondingly lower if the formulation is given in larger amounts. The formulations preferably comprise the indicated daily dose.

Unless otherwise indicated, data in % by weight are based on the total weight of the formulation.

The formulation base for novel formulations comprises physiologically acceptable excipients. Physiologically acceptable excipients are those known to be usable in the sectors of pharmacy, food technology and adjacent areas, in particular the excipients listed in relevant pharmacopeias (e.g. DAB, Ph. Eur., BP, NF), and other excipients whose properties do not stand in the way of physiological use. Excipients for the purposes of the invention may also have a nutritional value and are therefore generally used as food component. They may also include nutrients, especially essential nutrients.

Suitable excipients may be: wetting agents; emulsifying and suspending agents; preservatives; antioxidants; antiirritants; chelating agents; tablet coating aids; emulsion stabilizers; film formers; gel formers; odor-masking agents; masking flavors; resins; hydrocolloids; solvents; solubilizers; neutralizers; permeation promoters; pigments; quaternary ammonium compounds; refatting and superfatting agents; ointment, cream or oil bases; silicone derivatives; spreading aids; stabilizers; sterilants; suppository bases; tablet excipients such as binders, fillers, lubricants, disintegrants or coatings; propellants; desiccants; opacifiers; thickeners; waxes; plasticizers; white oils. An arrangement concerning this is based on specialist knowledge as described, for example, in Fiedler, H. P., Lexikon der Hilfsstoffe für Pharmazie, Kosmetik und angrenzende Gebiete, 4th edition, Aulendorf: ECV-Editio-Cantor-Verlag, 1996.

Food components usually comprise one or more amino acids, carbohydrates or fats and are suitable for the human and/or animal diet. They comprise individual components, frequently vegetable but also animal products, especially sugars, where appropriate in the form of syrups, fruit preparations such as fruit juices, nectar, fruit pulps, purees or dried fruit, for example apple juice, grapefruit juice, orange juice, apple purée, tomato sauce, tomato juice, tomato purée; cereal products such as wheat flour, rye flour, oat flour, corn flour, barley flour, spelt flour, corn syrup and starches from said cereals; dairy products such as milk protein, whey, yoghurt, lecithin and lactose.

Essential nutrients include, in particular, vitamins, provitamins, trace elements, amino acids and fatty acids. Essential amino acids which may be mentioned are isoleucine, leucine, lysine, methionine, phenylalanine, threonine, tryptophan and valine. They also include semiessential amino acids which must be given, for example, in periods of growth or deficiency states, such as arginine, histidine, cysteine and tyrosine. Trace elements which may be mentioned are: essential trace elements which have been proved to be necessary for humans and deficiency of which leads to manifestation of signs and symptoms: iron, copper, zinc, chromium, selenium, calcium, magnesium, potassium, lithium, cobalt, molybdenum, iodine, silicon, fluorine, manganese. Likewise elements whose function in humans is as yet inadequately verified: tin, nickel, vanadium, arsenic, manganese. Fatty acids essential for humans which may be mentioned are: linoleic acid and linolenic acid. A comprehensive list of vitamins is to be found in "Referenzwerte für die Nährstoffzufuhr", 1st edition, Umschau Braus Verlag, Frankfurt am Main, 2000, edited by the Deutsche Gesellschaft für Ernährung.

The total of active ingredient component and formulation base is usually 100% by weight.

Examples of suitable formulations for food supplementation are capsules, tablets, pills, powder sachets, liquid ampoules and bottles with stopper inserts, besides the drug forms mentioned below.

Examples of suitable pharmaceutical formulations are solid drug forms such as oral powders, dusting powders, granules, tablets, especially film-coated tablets, pastilles, sachets, cachets, sugar-coated tablets, capsules such as hard and soft gelatin capsules, suppositories or vaginal drug forms, semisolid drug forms such as ointments, creams, hydrogels, pastes or patches, and liquid drug forms such as solutions, emulsions, especially oil-in-water emulsions, suspensions, for example lotions, preparations for injection and infusion, eye drops and ear drops. It is also possible to use implanted delivery devices for administering active ingredients of the invention. Liposomes or microspheres may also be used.

Food formulations usually have the customary form and are preferably made available in the form of infant food, breakfast products, especially in the form of mueslis or bars, sports beverages, complete meals, especially in the framework of complete balanced diets, dietetic products such as diet drinks, diet meals and diet bars.

The formulations are preferably administered by the oral route, but they can also be administered, especially in the pharmaceutical sector, by the rectal, transdermal, subcutaneous, intravenous, intramuscular or intranasal route.

For producing the compositions, the active ingredients are usually mixed or diluted with a suitable excipient. Excipients may be solid, semisolid or liquid materials serving as vehicle, carrier or medium for the active ingredient. Admixture of other excipients takes place, if necessary, in a manner known per se. It is possible to carry out shaping steps, where appropriate in conjunction with mixing processes, e.g. a granulation, compression and the like.

The active ingredient components can in particular be formulated together. However, they also be initially processed separately and subsequently combined in a compartmented, e.g. multilayer pharmaceutical form. It is thus possible to take account of possible active ingredient incompatibilities and different active ingredient properties such as bioavailability, stability, solubility and the like.

The present invention is explained in more detail by means of the following examples without being restricted thereto.

EXAMPLE 1

Pharmaceutical Compositions
a) Soft Gelatin Capsules
(folic acid 6 mg+vitamin B6 50 mg vitamin B12 0.6 mg)

| Filling: | |
| --- | --- |
| folic acid | 6 mg |
| vitamin B6 | 50 mg |
| vitamin B12 | 0.6 mg |
| soybean oil (refined) | 440 mg |
| soybean lecithin (E322) | 50 mg |
| colloidal silica | 5 mg |
| Capsule shell: | |

| -continued | |
| --- | --- |
| gelatin | 303 mg |
| glycerol 85% | 87 mg |
| sorbitol 70% | 77 mg |
| purified water | 52 mg |
| iron oxide pigment brown 75 (E 172) | 3 mg | b) Tablet
(folic acid 5 mg+vitamin B6 45 mg+vitamin B12 0.5 mg)

| folic acid | 5 mg |
| --- | --- |
| vitamin B6 | 45 mg |
| vitamin B12 | 0.5 mg |
| lactose | 127.5 mg |
| magnesium stearate | 5 mg |
| talc | 23.75 mg |
| microcrystalline cellulose | 81 mg |

EXAMPLE 2

Patient with Chronic Renal Failure

A 42-year old man with terminal renal failure has undergone regular hemodialysis for 6 years. The homocysteine level was 38 μmol/l. On daily oral administration of 1 mg of folic acid, 1 mg of vitamin B12 and 100 mg of vitamin B6 to this man, the homocysteine level fell to 24.4 μmol/l after 8-weeks. No further reduction occurred during the subsequent 3 months, despite continuation of the therapy. On discontinuation of the therapy, the homocysteine level again rose to 38 μmol/l within 8 weeks.

On daily oral administration now of 5 mg of folic acid, 0.7 mg of vitamin B12 and 50 mg of vitamin B6, the homocysteine level fell to 12.6 μmol/l after therapy for 8 weeks.

EXAMPLE 3

Patient Receiving Cyclosporin Therapy

A 36-year old patient with severe, therapy-resistant psoriasis vulgaris received 2.5 mg of cyclosporin per kg of body weight each day. The homocysteine level was 47 μmol/l.

On daily oral administration of 1 mg of folic acid, 1 mg of vitamin B12 and 100 mg of vitamin B6 to this man, the homocysteine level fell to 2 8.6 μmol/l. On discontinuation of the therapy, the homocysteine level rose to 47 μmol/l again after 4 weeks.

Subsequent therapy with daily oral administration of 6 mg of folic acid, 0.6 mg of vitamin B12 and 50 mg of vitamin B6 led to a reduction in the homocysteine level to 14.2 μmol/l after 8 weeks.

On discontinuation of this therapy, the homocysteine level again rose to 47 μmol/l after 8 weeks.

Subsequent therapy with daily oral administration of 5 mg of folic acid, 0.8 mg of vitamin B12 and 50 mg of vitamin B6 led to a renewed fall in the homocysteine level to 14.2 μmol/l after 8 weeks.

The invention claimed is:

1. A method for the regulation of homocysteine levels comprising administering to a subject in need thereof an effective amount of a composition comprising:
   (a) folic acid or a physiologically acceptable salt thereof;
   (b) vitamin $B_6$ (pyridoxine), pyridoxal, pyridoxamine, or a physiologically acceptable salt thereof,
      wherein said pyridoxal has the formula:

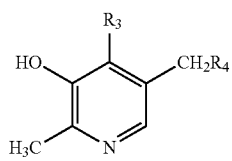

where $R_3$ is CHO and $R_4$ is OH
and wherein said pyridoxamine has the formula:

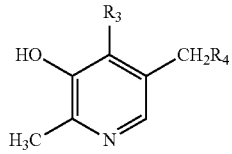

where $R_3$ is $CH_2NH_2$ and $R_4$ is OH and (c) vitamin $B_{12}$ (cyanocobalamine), hydroxocobalamin, methylcobalamin, or adenosylcobalamin, or a physiologically acceptable salt thereof, wherein the quantitative (a):(b) ratio is in a range of 1:5-15 by weight, the quantitative (c):(b) ratio is in a range of 1:50-125 by weight, and the quantitative (a):(c) ratio is in a range of 1:0.05-0.25 by weight, and wherein the effective amount is a daily dose ranging from 6 mg to 7 mg of (a), from 42 mg to 58 mg of (b) and from 0.7 mg to 0.8 mg of (c).

2. The method of claim 1, wherein said subject in need thereof is an individual suffering from renal failure or which is being treated with immunosuppressants.

3. The method of claim 1, wherein said method for the regulation of homocysteine levels is a method for the reduction of elevated homocysteine levels.

* * * * *